United States Patent
Inoue et al.

(10) Patent No.: US 9,678,337 B2
(45) Date of Patent: Jun. 13, 2017

(54) VIEWER WITH MULTIFOCAL LENS AND METHOD FOR CHANGING FOCAL LENGTH OF VIEWER

(71) Applicant: PANASONIC CORPORATION, Osaka (JP)

(72) Inventors: Tsuyoshi Inoue, Nara (JP); Yumiko Kato, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 283 days.

(21) Appl. No.: 14/284,982

(22) Filed: May 22, 2014

(65) Prior Publication Data

US 2014/0347623 A1 Nov. 27, 2014

(30) Foreign Application Priority Data

May 22, 2013 (JP) .................................. 2013-108022

(51) Int. Cl.
A61B 3/14 (2006.01)
G02B 27/00 (2006.01)
G02B 27/01 (2006.01)
A61B 3/00 (2006.01)

(52) U.S. Cl.
CPC ..... *G02B 27/0075* (2013.01); *G02B 27/0093* (2013.01); *G02B 27/017* (2013.01); *A61B 3/0091* (2013.01); *G02B 2027/0127* (2013.01); *G02B 2027/0187* (2013.01)

(58) Field of Classification Search
CPC ........ G02C 7/022; G02C 7/081; G02C 7/083; G02C 7/085; G02B 27/00; G02B 27/0068; G02B 27/0075

USPC .............. 351/209, 41, 159.01–159.03, 351/159.39–159.4
See application file for complete search history.

(56) References Cited

U.S. PATENT DOCUMENTS

2012/0236257 A1* 9/2012 Hillis ................. A61B 5/04001
351/205
2012/0310339 A1 12/2012 Berge

FOREIGN PATENT DOCUMENTS

| JP | 04-273211 A | 9/1992 |
| JP | 2010-262189 A | 11/2010 |
| JP | 2011-145358 A | 7/2011 |
| JP | 2013-513127 A | 4/2013 |

OTHER PUBLICATIONS

Yoshikazu Shinoda et al., "I Neurology of Eye Movement, 1 Type and Functional Sharing of Eye Movement," Neurology of Eye Movement Ed., p. 8, Igaku-Shoin, 1985. W/Partial English translation.

* cited by examiner

*Primary Examiner* — Scott J Sugarman
*Assistant Examiner* — Robert E Tallman
(74) *Attorney, Agent, or Firm* — McDermott Will & Emery LLP

(57) ABSTRACT

A viewer includes a multifocal lens capable of setting one of a plurality of focal lengths. When a measuring section detects a change in gazing point distance, a selection section selects a focal length to be set among the plurality of focal lengths, and a determiner determines a time duration before a focal length of the multifocal lens is changed. A controller changes the focal length of the multifocal lens when a detector detects a blink or saccadic eye movement of the user before the determined time duration elapses.

4 Claims, 8 Drawing Sheets

| GAZING POINT DISTANCE RANGE(cm) | FOCAL LENGTH(cm) |
|---|---|
| 0 OR MORE AND LESS THAN 30 | 20 |
| 30 OR MORE AND LESS THAN 100 | 60 |
| 100 OR MORE | 300 |

FIG.4

| GAZING POINT DISTANCE RANGE(cm) | FOCAL LENGTH(cm) | VIEWABILITY |
|---|---|---|
| ⋮ | ⋮ | ⋮ |
| 29 | 60 | 0.29 |
|  | 300 | 0 |
| 30 | 20 | 0.80 |
|  | 60 | 0.31 |
|  | 300 | 0 |
| 31 | 20 | 0.78 |
|  | 60 | 0.34 |
|  | 300 | 0 |
| ⋮ | ⋮ | ⋮ |

FIG.5

| VIEWABILITY DIFFERENCE | TIME DURATION (SEC.) |
|---|---|
| ⋮ | ⋮ |
| 0.42 OR MORE AND LESS THAN 0.44 | 0.6 |
| 0.44 OR MORE AND LESS THAN 0.46 | 0.5 |
| 0.46 OR MORE AND LESS THAN 0.48 | 0.5 |
| 0.48 OR MORE AND LESS THAN 0.50 | 0.4 |
| ⋮ | ⋮ |

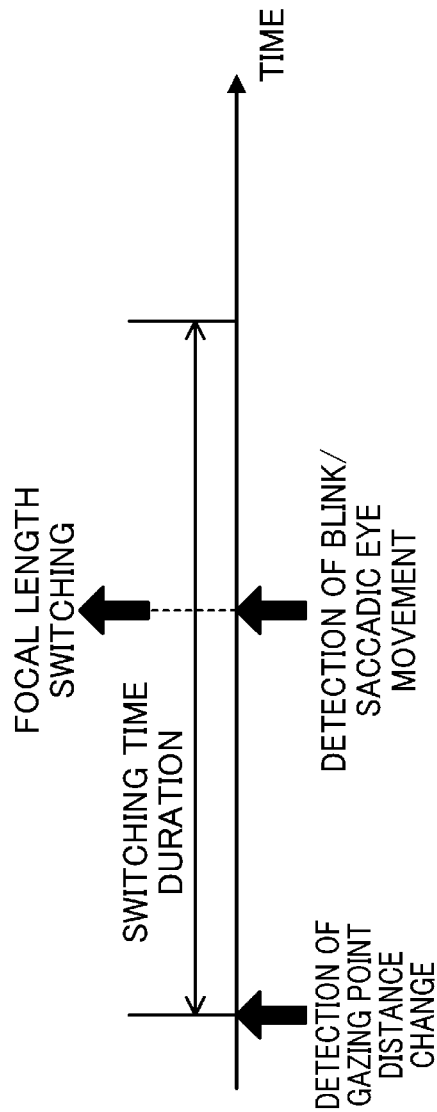
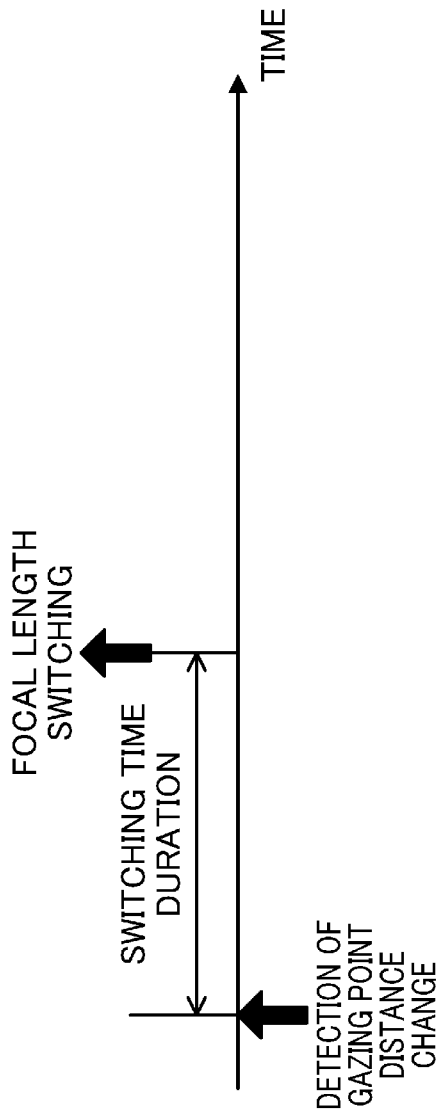

FIG.10

| CURRENT FOCAL LENGTH | GAZING POINT DISTANCE RANGE(cm) | SWITCHING FOCAL LENGTH | SWITCHING THRESHOLD VALUE(cm) |
|---|---|---|---|
| NEAR | 0 OR MORE AND LESS THAN 40 | NEAR | NO SWITCHING |
| | 40 OR MORE AND LESS THAN 100 | INTERMEDIATE | 40 |
| | 100 OR MORE | DISTANT | 100 |
| INTERMEDIATE | 0 OR MORE AND LESS THAN 25 | NEAR | 25 |
| | 25 OR MORE AND LESS THAN 120 | INTERMEDIATE | NO SWITCHING |
| | 120 OR MORE | DISTANT | 120 |
| DISTANT | 0 OR MORE TO 30 | NEAR | 30 |
| | 30 OR MORE TO 90 | INTERMEDIATE | 90 |
| | 90 OR MORE | DISTANT | NO SWITCHING |

FIG.11

| VIEWABILITY DIFFERENCE | SELECTED FOCAL LENGTH | TIME DURATION (SEC.) |
|---|---|---|
| ⋮ | ⋮ | ⋮ |
| 0.1 | DISTANT | 5.0 |
| 0.2 | NEAR | 0.5 |
| 0.2 | INTERMEDIATE | 1.0 |
| 0.2 | DISTANT | 5.0 |
| 0.3 | NEAR | 0.5 |
| ⋮ | ⋮ | ⋮ |

VIEWER WITH MULTIFOCAL LENS AND METHOD FOR CHANGING FOCAL LENGTH OF VIEWER

CROSS-REFERENCE TO RELATED APPLICATION

This application claims priority to Japanese Patent Application No. 2013-108022 filed on May 22, 2013, the entire disclosure of which is incorporated by reference herein.

BACKGROUND

The present disclosure relates to viewers that are equipped with multifocal lenses each having a plurality of focal lengths to be selected and are capable of adjusting focal lengths in accordance with distances of gazing points, i.e., points of fixation, of users.

To cope with abnormalities, such as myopia and presbyopia, in the accommodation ability, viewers having the function of automatically adjusting focal lengths, such as glasses and goggles using convex and concave lenses, have been proposed. Since we have a wide range of gazing point distance in daily live and a fixed focus lens has a narrow range of focal point, the use of multifocal lenses has been promoted for such a viewer. To adjust the focal length of a multifocal lens, it is necessary to know the gazing point (point of fixation) of the user.

Japanese Unexamined Patent Publication No. H04-273211 describes a technique of detecting a change in electro-oculogram occurring with eye movement in order to obtain a gazing point and adjusting the focal length of a varifocal lens in accordance with the gazing point.

Japanese Unexamined Patent Publication No. 2010-262189 proposes a technique of switching a focal length by automatic determination of a gazing point distance based on, for example, movement of a user in a viewer that switches among predetermined focal lengths.

SUMMARY

In a viewer with a multifocal lens having a plurality of focal lengths to be selected, in a case where the gazing point of a user is near a threshold value of switching determination among focal lengths, for example, the focal length of the viewer is frequently switched. In this case, an appearance, i.e., how the subject looks, is frequently changed or the subject is blurred by switching the focal length. Thus, the user feels strange or uncomfortable. That is, in a viewer with a multifocal lens that switches among a plurality of focal lengths, an appearance suddenly changes in switching the focal length, and thus, the user feels strange or uncomfortable.

It is therefore an object of the present disclosure to reduce strangeness or uncomfortableness of the user caused by switching among a plurality of focal lengths in a viewer with a multifocal lens having a plurality of focal lengths to be selected.

In an aspect of the present disclosure, a viewer includes: a multifocal lens capable of setting a focal length among a plurality of predetermined focal lengths; a controller that controls the focal length of the multifocal lens; a measuring section that measures a gazing point distance of a user and detects a change in the gazing point distance; a selection section that selects a focal length to be set among the plurality of focal lengths based on the measured gazing point distance when the measuring section detects a change in the gazing point distance; a determiner that determines a time duration from detection of a change in the gazing point distance to a change in the focal length of the multifocal lens in a case where the focal length selected by the selection section is different from a current focal length; and a detector that detects a blink or saccadic eye movement of the user, wherein in switching a focal length of the multifocal lens from the current focal length to the focal length selected by the selection section, the controller changes the focal length of the multifocal lens upon detection of a blink or saccadic eye movement by the detector during the time duration determined by the determiner from the detection of the change in the gazing point distance.

In this viewer, when the gazing point distance of the user changes and the selection section selects a focal length different from the current focal length, the determiner determines the time duration from detection of a change in the gazing point distance to a change in focal length of the multifocal lens. In switching the focal length of the multifocal lens, the controller changes the focal length of the multifocal lens upon detection of a blink or saccadic eye movement of the user during the time duration determined by the determiner from detection of a change in the gazing point distance. In this manner, switching the focal length of the multifocal lens is performed at the time of a blink or saccadic eye movement of the user, and thus, strangeness and uncomfortableness of the user caused by an abrupt change in focal length can be reduced.

According to the present disclosure, in a viewer capable of automatically adjusting the focal length of a lens in accordance with a gazing point distance of the user, strangeness and uncomfortableness of the user caused by an abrupt change in focal length can be reduced.

BRIEF DESCRIPTION OF THE DRAWINGS

FIG. 4 is an example of a table showing correspondence among the gazing point distance, the focal length, and the viewability.

FIG. 5 is an example of a table showing correspondence between the viewability difference and the time duration.

FIGS. 8A and 8B schematically show operation of switching the focal length in the embodiment, FIG. 8A shows operation when a blink, for example, is detected in a switching time duration, and FIG. 8B shows operation when a switching time duration has been elapsed without detection of a blink, for example.

FIG. 10 shows another example of correspondence between the gazing point distance and the focal length of a lens.

FIG. 11 is an example of a table showing correspondence among the viewability difference, the selected focal length, and the time duration.

DETAILED DESCRIPTION

Figure 1:
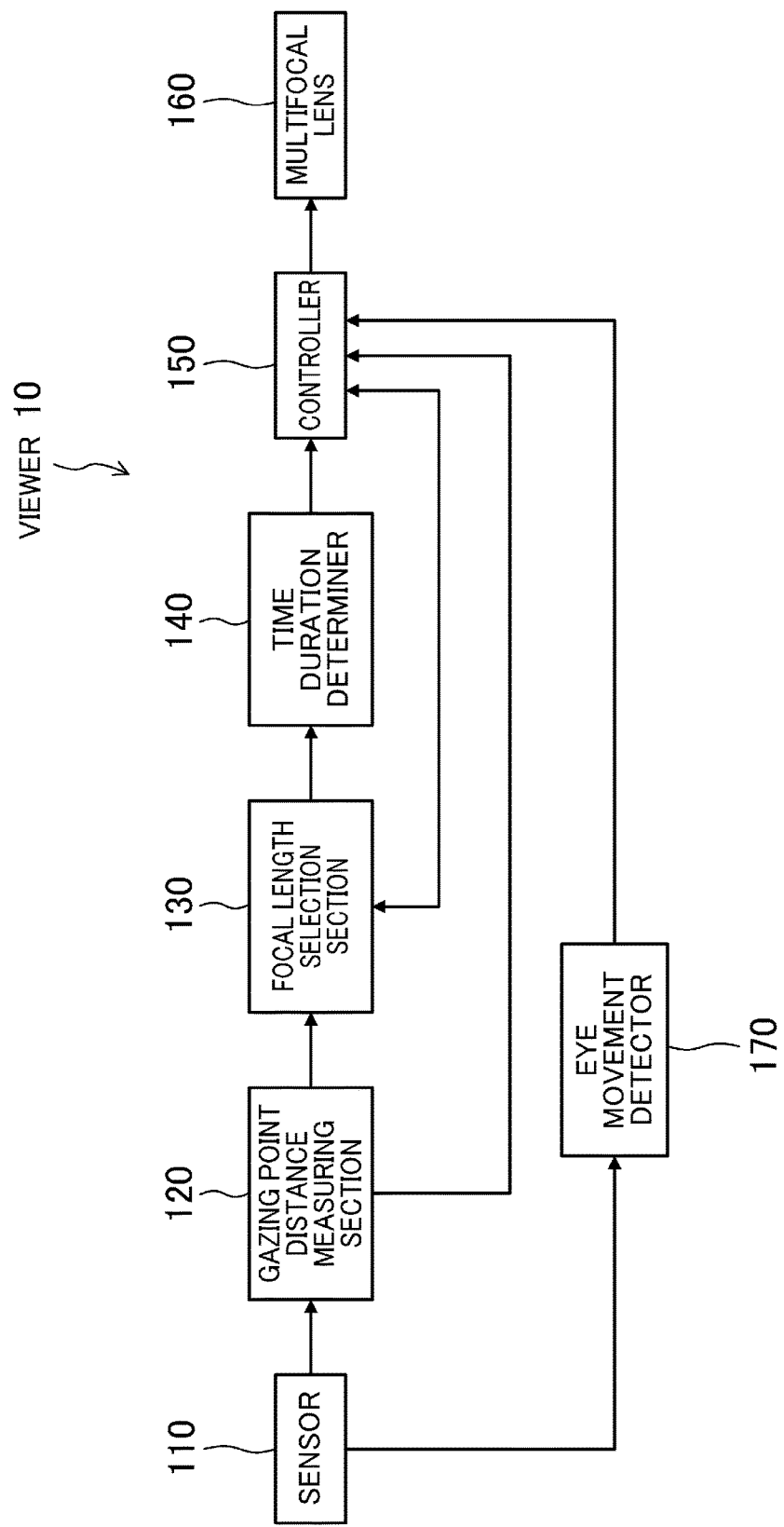
FIG. 1 is a block diagram showing an example configuration of a viewer according to an embodiment.

In a first aspect of the present disclosure, a viewer includes: a multifocal lens capable of setting a focal length among a plurality of predetermined focal lengths; a controller that controls the focal length of the multifocal lens; a measuring section that measures a gazing point distance of a user and detects a change in the gazing point distance; a selection section that selects a focal length to be set among the plurality of focal lengths based on the measured gazing point distance when the measuring section detects a change in the gazing point distance; a determiner that determines a time duration from detection of a change in the gazing point distance to a change in the focal length of the multifocal lens in a case where the focal length selected by the selection section is different from a current focal length; and a detector that detects a blink or saccadic eye movement of the user, wherein in switching a focal length of the multifocal lens from the current focal length to the focal length selected by the selection section, the controller changes the focal length of the multifocal lens upon detection of a blink or saccadic eye movement by the detector during the time duration determined by the determiner from the detection of the change in the gazing point distance.

In a second aspect of the present disclosure, in the viewer of the first aspect, the determiner includes a viewability estimation section that estimates, based on a given gazing point distance and a given focal length, a viewability index value indicating viewability in which the user sees the gazing point distance with the focal length being set, and the time duration is determined by using the viewability index value estimated by the viewability estimation section.

In a third aspect of the present disclosure, in the viewer of the second aspect, the determiner obtains, using the viewability estimation selection, a first index value that is a viewability index value based on the measured gazing point distance and the selected focal length and a second index value that is a viewability index value based on the measured gazing point distance and the current focal length, and determines the time duration based on a degree of change from the second index value to the first index value.

In a fourth aspect of the present disclosure, in the viewer of the third aspect, the determiner determines the time duration such that the time duration increases as the degree of change decreases.

In a fifth aspect of the present disclosure, in the viewer of the third aspect, the determiner determines the time duration such that the time duration is larger when the selected focal length is larger than the current focal length than when the selected focal length is smaller than the current focal length in a case where the degree of change is the same.

In a sixth aspect of the present disclosure, in the viewer of the third aspect, the determiner determines the time duration in consideration of the selected focal length in addition to the degree of change.

In a seventh aspect of the present disclosure, in the viewer of the second aspect, the viewability estimation section of the determiner obtains a viewability index value based on the measured gazing point distance and the current focal length, and determines the time duration such that the time duration increases as the viewability index value increases.

In an eighth aspect of the present disclosure, in the viewer of the first aspect, the determiner determines the time duration such that the time duration increases as the measured gazing point distance increases.

In a ninth aspect of the present disclosure, in the viewer of the first aspect, the determiner determines the time duration such that the time duration is larger when the selected focal length than the current focal length is larger than when the selected focal length is smaller than the current focal length.

In a tenth aspect of the present disclosure, in a method for changing a focal length of a multifocal lens in a viewer, the multifocal lens being capable of setting the focal length among a plurality of predetermined focal lengths, the viewer detects a change in a gazing point distance of a user, when a change in the gazing point distance is detected, the viewer selects the focal length to be set among the plurality of focal lengths based on a measured gazing point distance, when the selected focal length is different from a current focal length, the viewer determines a time duration from detection of a change in the gazing point distance to a change in the focal length of the multifocal lens, and in switching the focal length of the multifocal lens from the current focal length to the selected focal length, the viewer changes the focal length of the multifocal lens when a blink or saccadic eye movement of the user is detected during the determined time duration from the detection of the change in the gazing point distance.

These general or specific aspects may be implemented by systems, methods, integrated circuits, computer programs, or recording media such as computer-readable CD-ROMs, and may also be implemented by any combination of a system, a method, an integrated circuit, a computer program, and a recording media.

A viewer according to an embodiment of the present disclosure will be specifically described with reference to the drawings.

An embodiment described below is an example of the present disclosure. Values, shapes, components, locations and connection states of the components, steps, the order of states, etc. described in the following embodiment are examples, and are not intended to limit the scope of the invention. Among the components in the following description, components not recited in an independent claim represented the broadest concept will be described as optional components.

Reasons for switching the focal length of a multifocal lens upon a blink or saccadic eye movement will now be described.

In a viewer capable of adjusting the focal length, eye movement of the user is measured with a behavior in which the user visually perceives the outside and moves the gazing point to a subject in the field of view. That is, switching the focal length of the multifocal lens occurs when the user visually perceives the outside through the lens of the viewer. The eye movement herein refers to a behavior in which the user intentionally moves the gazing point, but the user is not conscious of this eye movement. Thus, the user is not conscious of the timing of automatically switching the focal length in accordance with the eye movement. The user feels an abrupt change of appearance: the focal length of the lens is unexpectedly changed in the middle of visual perception of the outside, a scene on which the focal point was fixed becomes suddenly blurred, and another scene on which the focal point was not fixed comes to be clearly seen abruptly. This abrupt change in the field of view causes strangeness to the user. A state of, for example, a loss of gazing point due to abrupt switching makes the switch of the focal length uncomfortable to the user.

This strangeness or uncomfortableness is caused by the following mechanism. While the user "sees," which means that a photic stimulation received by retina is transmitted to the brain and processed in the brain, the photic stimulation on the retina changes rapidly and, thereby, the information becomes discontinuous. On the other hand, a human sometimes moves the point of view quickly in daily life. For example, during driving of an automobile, the point of view is quickly moved to a signal light, a pedestrian, an oncoming car, or a sign. At this time, a scene during movement of the point of view is not "seen" by the user. That is, in eye movement, although photic stimulation of a quickly passing scene is input to retina, the user recognizes only inputs to retina at the times when the point of view is fixed before and after the movement of the point of view. Scenes that are blurred during passing are not perceived. In the visual system in the brain of a human, the threshold value increases in response to a visual input upon saccadic eye movement, and the sense of sight is suppressed (see, YOSHIKAZU SHINODA, "I Neurology of Eye Movement, 1 Type and Functional Sharing of Eye Movement," NEUROLOGY OF EYE MOVEMENT Ed. ATSUSHI KOMATSUZAKI, YOSHIKAZU SHINODA, and TOSHIO MARUO, P8, IGAKU-SHOIN, 1985). In addition, an eyelid is actually closed at a blink, and no stimulation on the sense of sight is input.

Strangeness due to an abrupt change in the focal length of the viewer is caused by a rapid artificial change of photic stimulation to retina. Thus, when the focal length of the viewer is switched upon saccadic eye movement or a blink in which a human does not physiologically "see" (i.e., the sense of sight is suppressed), the user often fails to recognize the rapid change caused by switching as seeing, i.e., the sense of sight. In this manner, by utilizing a physiological mechanism of a human to a rapid change of a retina image, strangeness or uncomfortableness in switching the focal length can be reduced without an additional load on the user.

In this specification, "saccadic eye movement" does not include eye movement in which the gazing point distance of the user changes, i.e., saccadic eye movement in the depth direction. When eye movement in the depth direction is detected, this eye movement is treated as a change in gazing point distance. In this specification, "saccadic eye movement" is eye movement in a case where there is no movement in the depth direction and the line-of-sight moves on a spherical surface or a planar surface at the same distance from the user.

First Embodiment

In a first embodiment, a viewer such as glasses or goggles, equipped with a multifocal lens and capable of adjusting the focal point in accordance with eye movement of a user will be described. The viewer of this embodiment can set one of a plurality of predetermined focal lengths, and in switching among the focal lengths, determines a time duration to actual switch of the focal length. Prior to a lapse of this time duration, the focal length is switched at the time of a blink or saccadic eye movement of the user.

FIG. 1 is a block diagram showing an example configuration of the viewer of this embodiment. A viewer 10 shown in FIG. 1 is configured to adjust the focal length in accordance with eye movement of the user, and includes a sensor 110, a gazing point distance measuring section 120, a focal length selection section 130, a time duration determiner 140, a controller 150, a multifocal lens 160, and an eye movement detector 170.

The multifocal lens 160 is a lens configured to set one of a plurality of predetermined focal lengths. Specifically, a plurality of focal lengths can be selected by adjusting a pressure on enclosed liquid or an enclosed gelled substance or by using a material with a specific refractive index relative to an electrical application such as liquid crystal. The focal length of the multifocal lens 160 is controlled based on a control signal of the controller 150.

The sensor 110 performs sensing for measuring a gazing point distance of the user. In the example of FIG. 1, the sensor 110 senses eye movement of the user. Examples of the sensor for sensing eye movement include cameras for capturing eyes and electro-oculogram sensors for recording potential changes on the skin in accordance with eye movement.

The gazing point distance measuring section 120 measures the gazing point distance, i.e., the distance from the eyes of the user to a position at which the user is gazing, based on data obtained by sensing of the sensor 110. Then, the gazing point distance measuring section 120 detects a change in gazing point distance.

The focal length selection section 130 selects a focal length to be set among a plurality of predetermined focal lengths that can be set in the multifocal lens 160, based on the gazing point distance of the user measured by the gazing point distance measuring section 120.

The eye movement detector 170 detects a blink or saccadic eye movement of the user based on information sensed by the sensor 110.

The time duration determiner 140 determines a time duration in which the timing of switching the focal length of the multifocal lens 160 can be set. Specifically, when the focal length selection section 130 selects a focal length different from a current focal length, the time duration determiner 140 determines a time duration from detection of a change in gazing point distance by the gazing point distance measuring section 120 to a change in focal length of the multifocal lens 160. In this time duration, when the eye movement detector 170 detects a blink or saccadic eye movement of the user, a change in focal length is executed. The time duration determiner 140 will be described specifically later.

The controller 150 controls the focal length of the multifocal lens 160, and outputs a control signal for switching the focal length. In the case of switching the focal length of the multifocal lens 160 from a current focal length to a selected focal length, the controller 150 changes the focal length of the multifocal lens 160 when a blink or saccadic eye movement is detected by the eye movement detector 170 in a period from detection of a change in gazing point distance to a lapse of the time duration determined by the time duration determiner 140. If neither a blink nor saccadic eye movement is detected until a lapse of the determined time duration, the focal length of the multifocal lens 160 is changed when the determined time duration elapses.

Here, it is assumed that the multifocal lens 160 can select three types of focal lengths as a plurality of focal lengths. A focal length of a lens for near view for use in, for example, reading is set at the closest position to the eyes of the user. The focal length of the lens for near view is, for example, 20 cm. A focal length of a lens for distant view for use in, for example, walking or driving is set at the farthest position from the eyes of the user. The focal length of the lens for distant view is, for example, 3 m. Between these focal lengths, a focal length of a lens for intermediate distance for use in, for example, work at hand or operation of a computer is set. The focal length of the lens for intermediate distance is, for example, 60 cm.

Figures 2, 3:
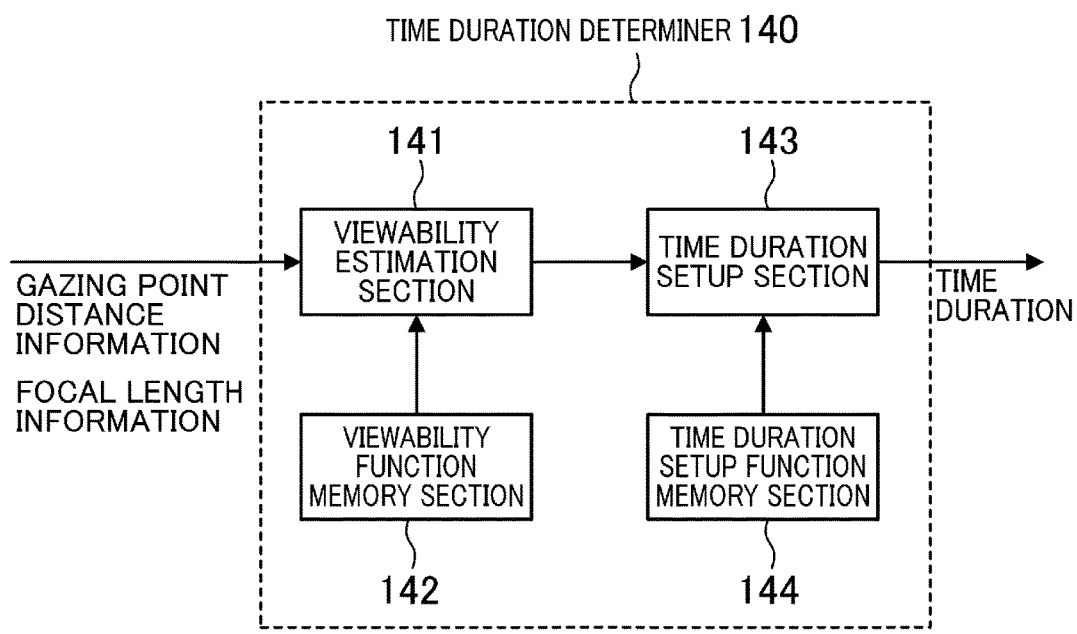
FIG. 2 shows an example of correspondence between the gazing point distance and the focal length of a lens.
FIG. 3 is a block diagram showing an example configuration of a time duration determiner in the viewer shown in FIG. 1 in detail.

FIG. 2 shows an example of correspondence between the gazing point distance and the focal length. In FIG. 2, if the gazing point distance is less than 30 cm, the focal length is set at 20 cm for near view. If the gazing point distance is 30 cm or more and less than 100 cm, the focal length is set at 60 cm for intermediate distance. If the gazing point distance is 100 cm or more, the focal length is set at 300 cm for distant view. The correspondence as shown in FIG. 2 is stored in, for example, the focal length selection section 130.

<Detail of Time Duration Determiner>

FIG. 3 is a block diagram showing an example configuration of the time duration determiner 140 in the viewer 10 shown in FIG. 1 in detail. The time duration determiner 140 shown in FIG. 3 includes a viewability estimation section 141, a viewability function memory section 142, a time duration setup section 143, and a time duration setup function memory section 144.

Based on a given gazing point distance and a given focal length, the viewability estimation section 141 estimates a viewability index value indicating viewability when the user sees the gazing point distance with the focal length being set. In this embodiment, a function for determining a viewability index value stored in the viewability function memory section 142 is used. This function is used for outputting a viewability index value when a gazing point distance and a focal length are given. Here, it is assumed that the output value of the function is one when the gazing point distance coincides with the focal length, and decreases toward zero as the gazing point distance gradually becomes away from the focal length.

The time duration setup section 143 sets a time duration by using the viewability index value estimated by the viewability estimation section 141. In this embodiment, the viewability estimation section 141 obtains a viewability index value (a first index value) based on the measured gazing point distance and the selected focal length, and a viewability index value (second index value) based on the measured gazing point distance and a current focal length. The time duration setup section 143 sets a time duration based on the difference between the first index value and the second index value. At this time, the function stored in the time duration function memory section 144 is used. This function is used for outputting the value of the time duration when the difference between the first index value and the second index value is given. In this embodiment, the output time duration increases as the difference decreases.

In this embodiment, the degree of change in viewability index value in switching the focal length is expressed as the difference between the first index value and the second index value. However, the present disclosure is not limited to this example. For example, the degree of change in viewability index value may be expressed as a ratio between the first index value and the second index value. That is, any operation may be employed as long as the degree of change from viewability with the current focal length to viewability with the selected focal length with respect to the measured gazing point distance is expressed.

In the configuration illustrated in FIG. 3, the function is used for obtaining a viewability index value. Alternatively, a table storing viewability index values corresponding to gazing point distances and focal lengths may be used. FIG. 4 shows an example of the table storing viewability index values corresponding to gazing point distances and focal lengths. If the table does not store a corresponding gazing point distance or focal length, a viewability index value can be obtained by interpolation using a viewability index value at an adjacent gazing point distance or focal length.

In the configuration shown in FIG. 3, the function is used for setting a time duration. Alternatively, a table storing a time duration corresponding to the degree of change in viewability index may be used, for example. FIG. 5 shows an example of a table storing a time duration corresponding to the difference in viewability index.

In the case of using the tables as shown in FIGS. 4 and 5, a time duration can be determined in, for example, the following manner. If the current focal length is 60 cm for intermediate distance and the measured gazing point distance is 30 cm, 20 cm for near view is selected as a new focal length. In this case, with reference to the table of FIG. 4, the index value of viewability is 0.31 before change, is 0.80 after the change, and the difference therebetween is 0.49. With reference to the table of FIG. 5, the time duration is 0.4 seconds.

The viewability index values corresponding to the gazing point distances and the focal lengths can be prepared in, for example, the following manner. A test type such as a Landolt ring is placed at a distance that is set as a gazing point distance, and the user wearing the viewer is subjected to a test similar to a visual activity test with the focal length of the viewer being set at a predetermined value. From the test result, a viewability index value at the gazing point distance and the focal length is determined Such a process is repeated with the gazing point distance and the focal length being varied.

Figure 6:
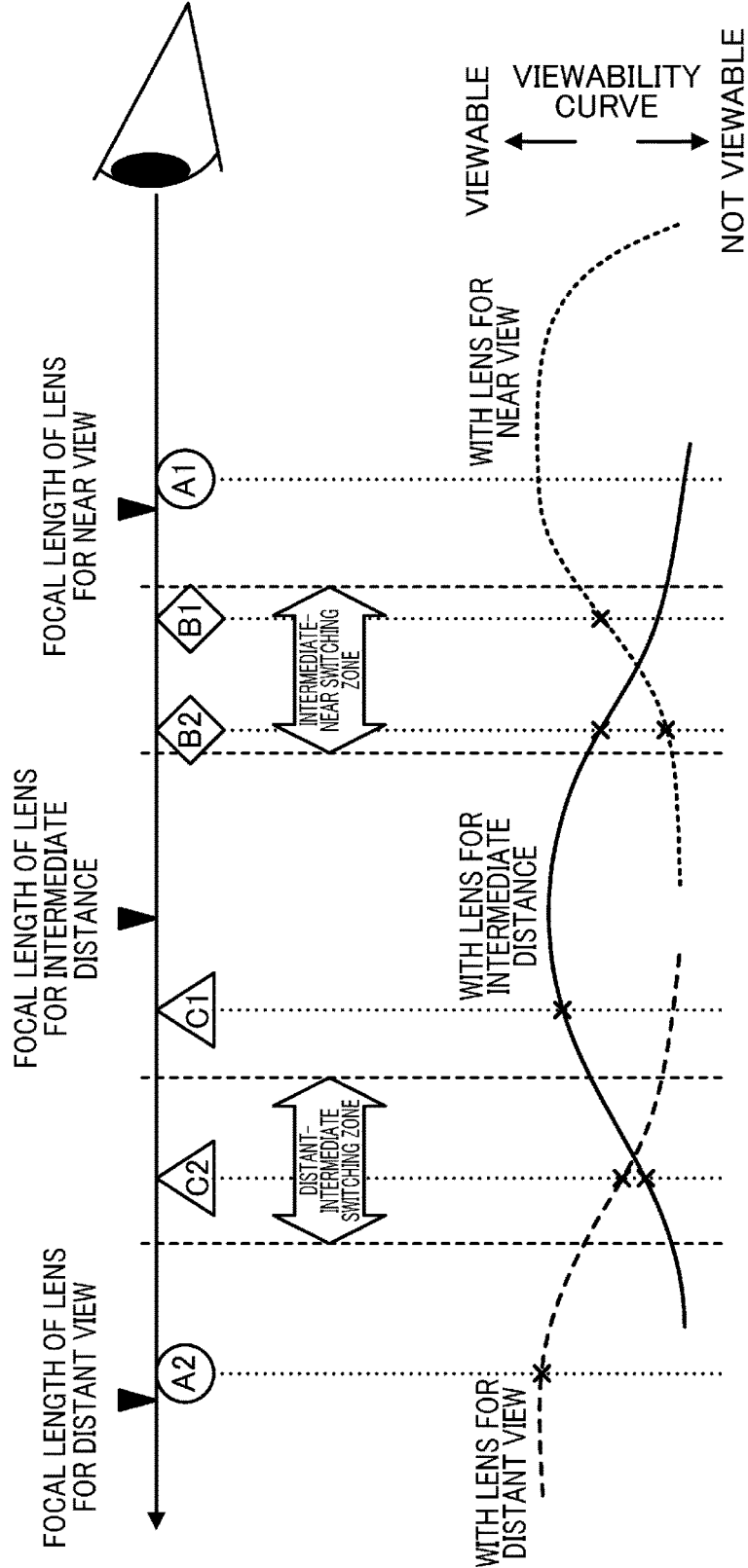
FIG. 6 schematically illustrates a relationship between lens selection depending on a gazing point distance and viewability of the user in the viewer of the embodiment.

FIG. 6 schematically illustrates a relationship between lens selection depending on the gazing point distance and viewability of the user in the viewer of this embodiment. In FIG. 6, a line indicating the gazing point distance with reference to the eye at the upper right corner is drawing, and settings of three types of focal lengths are shown on this line. Curves indicating viewability to the gazing point distance for focal lengths are schematically drawn at the bottom.

In FIG. 6, a pair of A1 and A2, a pair of B1 and B2, and a pair of C1 and C2 show examples of movement of the gazing point distance. In movement from A1 to A2, the gazing point distance moves from a position at a distance of 18 cm to a position at a distance of 2.8 m from the user's eye, for example. At A2, viewability in the case of using a lens for distant view is approximately at maximum, i.e., most viewable, and no high viewabilities are obtained with the other lenses. Thus, in the movement of the gazing point distance from A1 to A2, an advantage of high viewability obtained by switching the focal length is more than strangeness or uncomfortableness caused by switching the focal length. Accordingly, prompt switching the focal length is preferable to the user. In such a case, it is preferable to switch the focal length of a lens at the time of, for example, detection of movement of the gazing point distance without a wait time, irrespective of whether there is a blink or saccadic eye movement or not.

In movement from B1 to B2, the gazing point distance moves from a position at a distance of 28 cm to a position at a distance of 40 cm from the user's eye, for example. At B1, a lens for near view is used. This is because viewability with the lens for near view is higher than that with a lens for intermediate distance at B1. At B2, viewability with the lens for near view used at B1 decreases, whereas viewability in the case of using the lens for intermediate distance increases. That is, the viewability order is reversed. Note that viewability in the case of using the lens for intermediate distance is not as high as that in a case where the gazing point distance is near the focal length. In such a case, the focal length is switched, but it is preferable that a time duration is set such that switching is performed at the time of occurrence of a blink or saccadic eye movement in this time duration in consideration of strangeness caused by switching the focal length and the degree of viewability obtained by switching the focal length. In this example, since the viewability difference between before and after switching the focal length is relatively large, a relatively small time duration is set.

On the other hand, in movement from C1 to C2, the gazing point distance moves from a position at a distance of 70 cm to a position at a distance of 1.5 m from the user's eye, for example. At C2, viewability with the lens for intermediate distance used at C1 before the movement decreases slightly below viewability in the case of using the lens for distant view. Note that at C2, viewability is not significantly high in both cases of using the lens for intermediate distance and using the lens for distant view. In such a case, although viewability is not significantly increased with switching the focal length, strangeness due to switching the focal length occurs. Thus, in a manner similar to the movement from B1 to B2, it is preferable that a time duration is set such that switching is performed at the time of occurrence of a blink or saccadic eye movement in this time duration. In this case, since the viewability difference between before and after switching the focal length is small, a relatively large time duration is set. Thus, the user can wait in a relatively long period for the time of detection of a blink or saccadic eye movement, and the focal length is switched without strangeness. If the viewability difference is smaller than a predetermined threshold value, no switching the focal length may be performed.

In this embodiment, switching the focal length is performed in the manner described above. In an actual application, an additional change in gazing point distance can be detected in the time duration determined for switching the focal length in some cases. Thus, determination of whether to perform switching the focal length and additional setting of the time duration may be performed at every detection of a change in gazing point distance. In this case, even in a case where the gazing point of the user frequently changes, the frequency of switching the focal length does not excessively increase, and strangeness and uncomfortableness caused by switching the focal length can be reduced.

Figure 7:
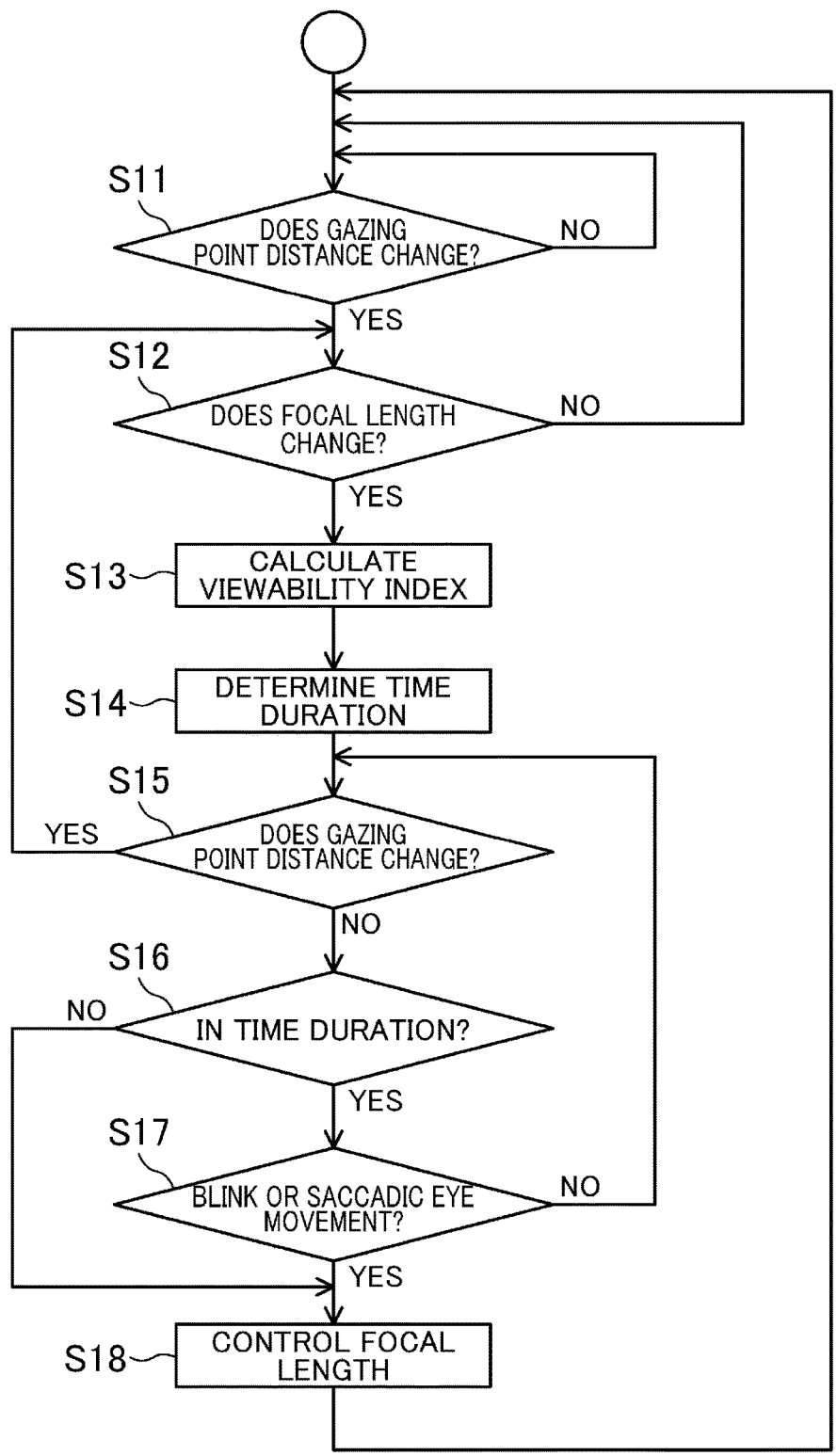
FIG. 7 is a flowchart showing an example of operation of the viewer of the embodiment.

FIG. 7 is a flowchart showing an example of operation of the viewer 10 of this embodiment. Referring to FIG. 7, a process flow of changing the focal point in the viewer 10 will be described.

First, the sensor 110 acquires the state of eyeballs of the user, and the gazing point distance measuring section 120 detects a change in gazing point distance of the user based on the data acquired by the sensor 110 (S11). If the change in gazing point distance is detected (YES at S11), the process proceeds to step S12. On the other hand, if the change in gazing point distance is not detected (NO at S11), step S11 is repeated.

At step S12, the focal length selection section 130 selects a new focal length based on a new gazing point distance measured by the gazing point distance measuring section 120 at step S11, in accordance with a predetermined relationship between the gazing point distance and the focal length as shown in, for example, FIG. 2. It is then determined whether the selected focal length is different from a current focal length stored in the controller 150 or not (S12). If the current focal length is different from the selected focal length, i.e., a change in focal length is performed (YES at S12), the process proceeds to step S13. On the other hand, if the current focal length is equal to the selected focal length, i.e., a change in focal length is not performed (i.e., NO at S12), the process returns to step S11.

At step S13, the time duration determiner 140 obtains viewability index values corresponding to the current focal length and the new focal length for the gazing point distance measured at step S11. In addition, at step S14, the time duration determiner 140 determines a time duration in which the viewer waits for a blink or saccadic eye movement in order to switch the focal length, by using the viewability index values obtained at step S13.

Specifically, steps S13 and S14 are performed by the time duration determiner 140 shown in FIG. 3 as described below, for example. At step S13, based on the function stored in the viewability function memory section 142, the viewability estimation section 141 obtains a viewability index value at the gazing point distance measured at step S11 for each of the focal length selected at step S12 and the current focal length. At step S14, the time duration setup section 143 obtains the difference or ratio between a viewability index value (a first index value) at the focal length selected at step S13 and a viewability index value (a second index value) at the current focal length. Then, based on the function stored in the time duration function memory section 144, the time duration setup section 143 obtains a time duration corresponding to the difference or ratio in viewability index. This function is a function that is zero seconds when the difference in viewability index value is one, and approaches five seconds as the difference in viewability index value approaches zero, for example. Alternatively, the function may be a function that is zero when the ratio in viewability index value is zero seconds, and approaches five seconds as the ratio in viewability index value approaches one.

At step S15, the controller 150 refers to the gazing point distance measuring section 120, and determines whether there is a change in gazing point distance of the user or not, in a manner similar to step S11. If there is a change in gazing point distance (YES at S15), the process returns to step S12. That is, it is determined whether there is switching the focal length or not and a time duration is set again. On the other hand, if there is not a change in gazing point distance (NO at S15), the process proceeds to step S16.

At step S16, the controller 150 determines whether the present time is in the time duration determined at step S14 or not. If the present time is still in the time duration (YES at S16), the process proceeds to step S17. At step S17, the controller 150 refers to the eye movement detector 170, and determines whether a blink or saccadic eye movement of the user is detected or not. If a blink or saccadic eye movement is detected (YES at S17), the process proceeds to step S18. If neither a blink nor saccadic eye movement is detected (NO at S17), the process returns to step S15. On the other hand, the present time has already passed the time duration (NO at S16), the process proceeds to step S18.

At step S18, the controller 150 outputs a control signal for switching the focal length of the multifocal lens 160 to the focal length selected at step S12, and the focal length of the multifocal lens 160 is switched.

FIGS. 8A and 8B schematically show operation at steps S16-S18. FIG. 8A shows operation in the case of YES at step S17, i.e., when a blink or saccadic eye movement is detected in a switching time duration determined at step S14. FIG. 8B shows operation in the case of NO at step S16, i.e., when a switching time duration elapses without detection of a blink or saccadic eye movement. As shown in FIG. 8A, when a blink or saccadic eye movement is detected in a switching time duration, the controller 150 promptly switches the focal length of the multifocal lens 160. On the other hand, as shown in FIG. 8B, when a switching time duration elapses without detection of a blink or saccadic eye movement, the controller 150 switches the focal length of the multifocal lens 160 at the time when the switching time duration has elapsed.

The foregoing series of operation at steps S11-S18 is repeated so that the viewer 10 of this embodiment can continuously perform operation of switching the focal length in accordance with a change in gazing point distance of the user with reduction of strangeness and uncomfortableness caused by switching the focal point.

In this example, operation of step S15 is the same as that of step S11, but is performed in a case where the gazing point distance further changes in a period from change in gazing point distance to switching the focal length of the multifocal lens. At step S15, if a change in gazing point distance is detected, the process proceeds to step S12. Thus, the focal length of the multifocal lens can be promptly switched to a focal length corresponding to the latest gazing point distance. In addition, the focal length is not frequently switched upon a small change in focal length.

As described above, in this embodiment, in the viewer 10 equipped with the multifocal lens 160 having a plurality of focal lengths to be set and capable of adjusting the focal length in accordance with eye movement of the user, when the gazing point distance of the user changes and a new focal length different from the current focal length is selected, the time duration determiner 140 determines a time duration before a change in focal length, based on the degree of change in viewability index value caused by switching the focal length. When the eye movement detector 170 detects a blink or saccadic eye movement of the user during the determined time duration, the controller 150 changes the focal length of the multifocal lens 160. In this manner, switching the focal length of the multifocal lens 160 is performed at the time of a blink or saccadic eye movement of the user, and thus, strangeness or uncomfortableness of the user due to an abrupt change of viewability caused by switching the focal length can be reduced.

Figure 9:
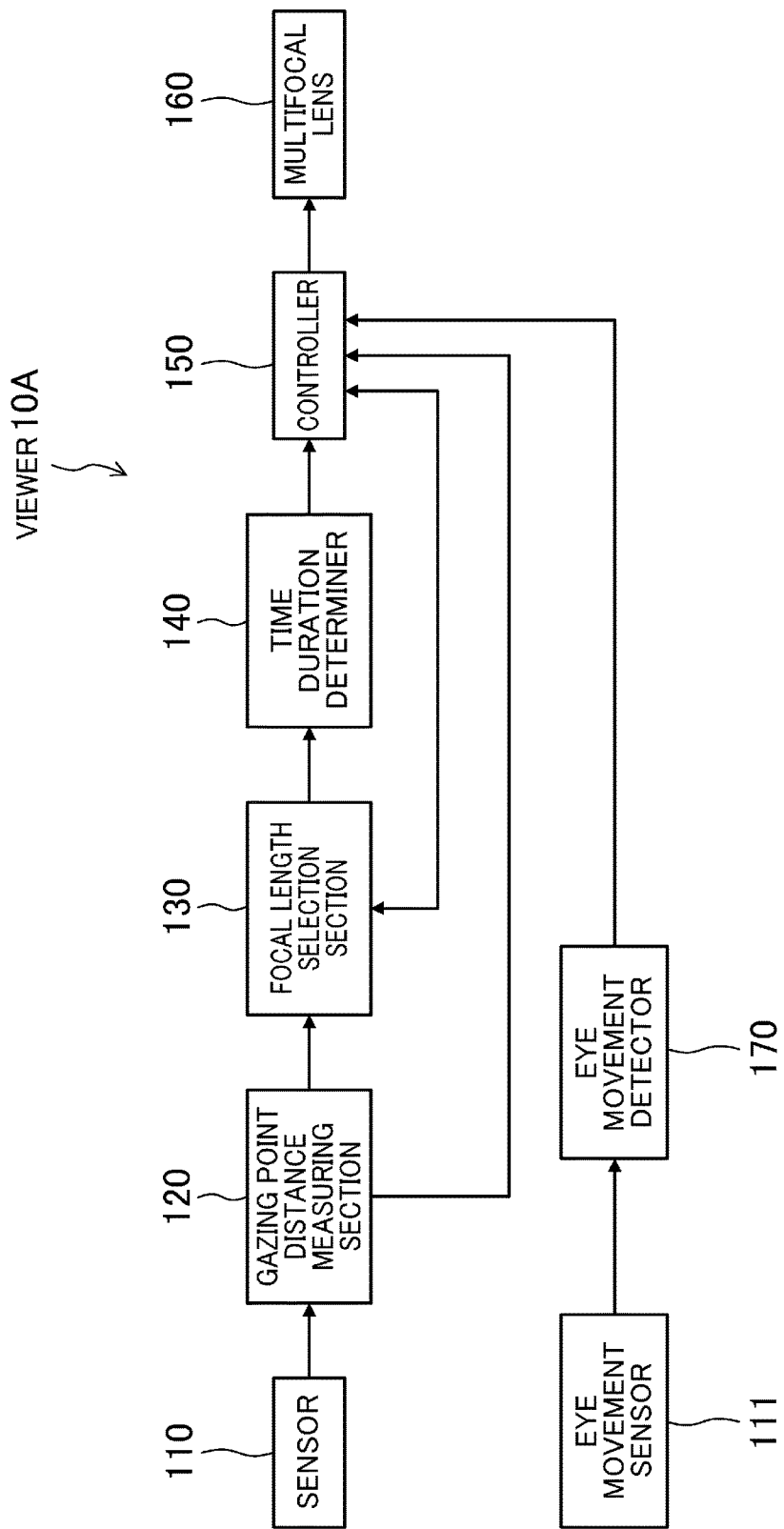
FIG. 9 is a block diagram showing another example configuration of the viewer of the embodiment.

In the configuration of FIG. 1, each of the gazing point distance measuring section 120 and the eye movement detector 170 utilizes an output of the sensor 110. On the other hand, as in a viewer 10A illustrated in FIG. 9, different sensors may be used as a sensor for performing sensing necessary for measuring a gazing point distance and a sensor for performing sensing for detecting a blink or saccadic eye movement. In the configuration of FIG. 9, an eye movement sensor 111 different from the sensor 110 is provided as a sensor for detecting a blink or saccadic eye movement. Specifically, the eye movement sensor 111 is a camera for capturing eyes or an electro-oculogram sensor for electrically measuring eye movement, for example. In the configuration of FIG. 9, the sensor 110 serving as a sensor for measuring a gazing point distance may be specifically a camera or an electro-oculogram sensor as described above or may be an infrared sensor using reflection of infrared light or an acceleration sensor for measuring an inclination.

In this embodiment, the focal length selection section 130 selects a focal length in accordance with correspondence between the gazing point distance and the focal length as shown in FIG. 2. Alternatively, a reference for switching the focal length may be set differently depending on the current focal length, for example.

FIG. 10 shows an example of correspondence between the gazing point distance and the focal length. In this example, a threshold value of switching the focal length varies depending on a current focal length. For example, in a case where the current focal length is a focal length for near view, the focus length is switched to a focal length for intermediate distance when the gazing point distance moves away to 40 cm or more. On the other hand, in a case where the current focal length is a focal length for intermediate distance, the focal length is not switched to a focal length for near view unless the gazing point distance approaches 25 cm or less.

In accordance with the correspondence as shown in FIG. 10, in a case where the gazing point distance approaches the user more closely than the current focal length, the focal length is switched after the gazing point distance becomes sufficiently small, whereas in a case where the gazing point distance moves away from the user and is located farther from the user than the current focal length is, the focal length is switched after the gazing point distance becomes sufficiently large. That is, the range of the gazing point distance in which the current focal length is selected is large in both of the cases where the gazing point distance decreases and where the gazing point distance increases. In this manner, the current focal length is readily maintained, and thereby, frequently switching the focal length caused by a small change in gazing point distance can be reduced. That is, by giving high priority to the current focal length, strangeness and uncomfortableness are less likely to occur upon switching the focal length.

In this embodiment, a time duration in which the viewer waits for a blink or saccadic eye movement in order to switch the focal point is determined in accordance with the correspondence between the degree of change in viewability index value and the time duration as shown in FIG. 5. On the other hand, the time duration may be determined based on other factors as well as the degree of change in viewability index value.

For example, the time duration may be determined based on a selected focal length in addition to the degree of change in viewability index value. FIG. 11 shows an example of correspondence among the viewability difference, the selected focal length, and the time duration. In FIG. 11, with the same viewability difference, the time duration is small in switching to a focal length for near view, and the time duration is large in switching to a focal length for distant view. In switching to a focal length for intermediate distance, the time duration has a value between a value in switching to the focal length for near view and a value in switching to the focal length for distant view.

In this manner, the focal length is promptly changed when the line-of-sight shifts to, for example, small characters at hand such as a document or a map, whereas the focal length is switched at the time of occurrence of a blink or saccadic eye movement in a large time duration when the line-of-sight shifts to a large television screen or scenery through a window, for example. Thus, strangeness and uncomfortableness caused by an abrupt change in the focal length can be reduced. That is, the focal length is promptly adjusted in a situation in which a subject at hand needs to be clearly seen in detail. On the other hand, in a situation where low viewability can be negligible in seeing a wide view, strangeness and uncomfortableness caused by switching the focal length can be reduced.

The time duration may be determined in consideration of whether the selected focal length is larger than the current focal length or not, in addition, the degree of change in viewability index value. Specifically, the time duration is changed depending on whether the focal length moves away from the user or approaches the user. For example, with the same viewability difference, the time duration is determined to be larger when the selected focal length is larger than the current focal length, i.e., the focal length moves away from the user, than when the selected focal length is smaller than the current focal length, i.e., the focal length approaches the user. Thus, the focal length is promptly adjusted when the user moves the line-of-sight to a close position, and the focal length is switched at the time of occurrence of a blink or saccadic eye movement when the user moves the line-of-sight to a distant position, thereby reducing strangeness and uncomfortableness caused by switching the focal length.

Instead of, or in addition to, the degree of change in viewability index value, the viewability index value itself may be used for determining a time duration. For example, a viewability index value is obtained based on a measured gazing point distance and a current focal length, and a time duration is determined such that the time duration increases as the viewability index value increases. Thus, in a case where viewability does not significantly decrease with the current focal length, the time duration is determined to be relatively large so that the viewer can wait for the time of occurrence of a blink or saccadic eye movement. As a result, strangeness and uncomfortableness caused by an abrupt change in focal length can be reduced.

A time duration may be determined by not using a viewability index but based on other conditions. For example, the time duration may increase as the measured gazing point distance increases. In this case, the focal length is promptly adjusted when the user sees a subject nearby, and the focal length is switched at the time of occurrence of a blink or saccadic eye movement when the user sees a subject far from the user. In this manner, strangeness and uncomfortableness caused by switching the focal length can be reduced.

Alternatively, the time duration may be determined based on whether a selected focal length is larger than a current focal length or not. Specifically, the time duration is changed depending on whether the focal length moves away from the user or approaches the user. For example, the time duration is determined to be larger when the selected focal length is larger than the current focal length, i.e., the focal length moves away from the user, than when the selected focal length is smaller than the current focal length, i.e., the focal length approaches the user. Thus, the focal length is promptly adjusted when the user moves the line-of-sight to a close position, and the focal length is switched at the time of occurrence of a blink or saccadic eye movement when the user moves the line-of-sight to a distant position, thereby reducing strangeness and uncomfortableness caused by switching the focal length.

In the above embodiment, the focal length is switched at the time when the eye movement detector 170 detects a blink or saccadic eye movement. The time at which the focal length is switched includes the case of using both a blink and saccadic eye movement, the case of using only a blink, the case of using only saccadic eye movement, and the case of selectively using a blink or saccadic eye movement depending on situations, for example.

<Supplemental Description for Practical Use>

In the foregoing embodiment, the focal length of the multifocal lens 160 is switched upon occurrence of a blink or saccadic eye movement. In this case, the switching the focal length of the multifocal lens 160 is preferably finished within a period of a blink or saccadic eye movement. In a case where the multifocal lens 160 is a liquid crystal lens, the time necessary for switching the focal length is tens milliseconds. On the other hand, a blink takes about 200 milliseconds from the start to the end of the blink. Saccadic eye movement takes about several tens milliseconds to about 100 milliseconds from the start to the end of the movement in a short case. In a case where the time necessary for completing switching the focal length of the multifocal lens 160 is about 50 milliseconds including processing and control of the lens, if the sensor 110 is a camera, several samples of images necessary for detecting a blink or saccadic eye movement needs to be acquired within about 50 milliseconds. For example, in a case where about three or four samples of images are needed for detecting a blink or saccadic eye movement, one sample of an image needs to be acquired within a period from 12 milliseconds to 16 milliseconds. In the case of a camera with a sampling frequency of 60 Hz, the sampling interval is about 16 milliseconds, and in this case, the focal length can be switched within a period of a blink or saccadic eye movement.

In general, in detecting saccadic eye movement with an image sensor, a pupil center is extracted from images, and when the pupil center moves in a distance of a predetermined value or more among the images, it is determined that saccadic eye movement occurs. However, in application of the present disclosure to an actual device, an initial stage of saccadic eye movement needs to be detected early in some cases. The speed of saccadic eye movement is considered to about 350-500 degrees per a second where the rotation angle of an eye is within about 20 degrees (see YOSHIKAZU SHINODA, "I Neurology of Eye Movement, 1 Type and Functional Sharing of Eye Movement," NEUROLOGY OF EYE MOVEMENT Ed. ATSUSHI KOMATSUZAKI, YOSHIKAZU SHINODA, and TOSHIO MARUO, P8, IGAKU-SHOIN, 1985), the speed of saccadic eye movement is similar, irrespective of the focal length. However, when the rotation angle of an eyeball further increases, the speed of eye movement also increases.

In this disclosure, saccadic eye movement is defined as movement of a gazing point on a planar surface at a constant gazing point distance. Specifically, the movement includes movement to an index on a planar surface of a book in reading, movement to an index on a planar surface of a signboard in seeing a distant signboard, etc. In these cases, when the gazing point distance is small, the planar surface at the same gazing point distance is small in area, such as a book or a cell phone. That is, the eye movement angle of saccadic eye movement is small, and the speed of the eye movement is within a constant range. When the gazing point moves out of the planar surface of, for example, a book, the gazing point distance changes. On the other hand, in a case where the gazing point distance is large, e.g., a case where the line-of-sight shifts from a signboard or a signal light at an intersection to a sign, the movement distance of the gazing point on the same planar surface is large, i.e., the rotation angle of eyes is large. Thus, the speed of eye movement is often higher than that in the case of a small gazing point distance.

When saccadic eye movement is started, the threshold value of saccadic eye movement needs to be change depending on the focal length in order to determine that saccadic eye movement is started promptly. Thus, for example, in the eye movement detector 170 of the above embodiment, different threshold values are set for different movement distances of the pupil center in accordance with the focal length, thereby enabling earlier detection of a start of saccadic eye movement.

In the case of detecting a blink by using an image sensor, a blink is detected based on whether a pupil is covered with an eyelid or not. However, to detect a blink in an early stage, it is necessary to detect a situation where a pupil is partially covered. In view of this, for example, in the eye movement detector 170 of the above embodiment, reference images in which a pupil is partially covered with an eyelid are prepared, and a similarity with the reference images is detected. Then, a start of a blink can be detected earlier. Since the reference images in which a pupil is partially covered with an eyelid differ among individuals, images after users wear viewers are accumulated, and a reference image is extracted from the accumulated images. Then, the viewer can cope with individual images.

The present disclosure is widely applicable to optical systems using multifocal lenses, e.g., optical systems that adjust focal lengths including viewers such as glasses and goggles, microscopes, binoculars, head-mounted displays, etc., and is useful for adjusting the focal lengths of viewers, microscopes, binoculars, head-mounted displays, etc.

What is claimed is:

1. A viewer comprising:
   a multifocal lens capable of setting a focal length among a plurality of predetermined focal lengths;
   a controller that controls the focal length of the multifocal lens;
   a measuring section that measures a gazing point distance of a user and detects a change in the gazing point distance, the gazing point distance being the distance from the eyes of a user to a position at which the user is gazing;
   a selection section that selects a focal length to be set among the plurality of focal lengths based on the measured gazing point distance when the measuring section detects a change in the gazing point distance;
   a determiner that determines a time duration from detection of a change in the gazing point distance to a change in the focal length of the multifocal lens in a case where the focal length selected by the selection section is different from a current focal length; and
   a detector that detects a blink or saccadic eye movement of the user, wherein
   in switching the focal length of the multifocal lens from the current focal length to the focal length selected by the selection section, the controller changes the focal length of the multifocal lens upon detection of a blink or saccadic eye movement by the detector during the time duration determined by the determiner from the detection of the change in the gazing point distance.

2. The viewer of claim 1, wherein the determiner determines the time duration such that the time duration increases as the measured gazing point distance increases.

3. The viewer of claim 1, wherein the determiner determines the time duration such that the time duration is larger when the selected focal length is larger than the current focal length than when the selected focal length is smaller than the current focal length.

4. A method for changing a focal length of a multifocal lens in a viewer, the multifocal lens being capable of setting the focal length among a plurality of predetermined focal lengths, the method comprising the steps of:
   detecting a change in a gazing point distance of a user by the viewer, the gazing point distance being the distance from the eyes of a user to a position at which the user is gazing,
   selecting the focal length to be set among the plurality of focal lengths based on a measured gazing point distance by the viewer when a change in the gazing point distance is detected,
   determining a time duration from detection of a change in the gazing point distance to a change in the focal length of the multifocal lens by the viewer when the selected focal length is different from a current focal length, and
   changing the focal length of the multifocal lens by the viewer when a blink or saccadic eye movement of the user is detected during the determined time duration from the detection of the change in the gazing point distance, in switching the focal length of the multifocal lens from the current focal length to the selected focal length.

* * * * *